United States Patent [19]

Tochikura et al.

[11] Patent Number: 4,990,450
[45] Date of Patent: Feb. 5, 1991

[54] METHOD OF PRODUCING ENDO-α-N-ACETYLGALACTOSAMINIDASE FROM MICROORGANISMS

[75] Inventors: Tatsurokuro Tochikura, Muko; Hidehiko Kumagai; Kenji Yamamoto, both of Otsu; Setsu Kadowaki, Kyoto, all of Japan

[73] Assignee: Seitetsu Kagaku Co., Ltd., Hyogo, Japan

[21] Appl. No.: 189,135

[22] Filed: May 2, 1988

[30] Foreign Application Priority Data

May 7, 1987 [JP] Japan .................. 62-112059

[51] Int. Cl.$^5$ .................. C12N 9/24; C12P 19/44; C12R 1/05
[52] U.S. Cl. .................. 435/200; 435/74; 435/829
[58] Field of Search .................. 435/200, 829, 68, 74, 435/71.2

[56] References Cited

PUBLICATIONS

Bergey's Manual of Determinative Bacteriology, 8th Edition, 1974, (R. E. Buchanan & N. E. Gibbons ed. 5), pp. 273–275.

Yamamoto K., et al., (1987), Agric. Biol. Chem. 51(11), 3169–3171.
Fan, J. Q., et al., (1988) Agric. Biol. Chem. 52(7), 1715–1723.
V. P. Bhavanandan et al., Biochemical and Biophysical Research Communications, vol. 70, No. 3, 1976, 738–745.
Yoshinori Endo et al., J. Biochem., 80, 1–8, (1976).
Lowrie R. Glasgow, et al., The Journal of Biological Chemistry, vol. 252, No. 23, pp. 8615–8623, 1977.
Junji Umemoto, et al., The Journal of Biological Chemistry, vol. 252, No. 23, pp. 8609–8614, 1977.

Primary Examiner—Elizabeth C. Weimar
Assistant Examiner—Charles L. Patterson, Jr.
Attorney, Agent, or Firm—Irell & Manella

[57] ABSTRACT

This invention provides endo-α-N-acetylgalactosaminidase (endo-α-GalNAcase) from a microorganism belonging to the genus Alcarigenes. This endo-α-GalNAcase is very useful in the analysis of the structure and function of mucin-type sugar chains of glycoproteins, as it is an enzyme that cleaves O-glycosidic linkages of sugar chains of glycoproteins, releasing the sugar chain from said protein.

2 Claims, No Drawings

METHOD OF PRODUCING ENDO-α-N-ACETYLGALACTOSAMINIDASE FROM MICROORGANISMS

BACKGROUND OF THE INVENTION

1. Field of the Invention

This invention relates to a method of producing endo-α-N-acetylgalactosaminidase from microorganisms.

2. Description of the Prior Art

In recent years, it has been found the important functions of the sugar-chain portions of complex carbohydrates for cell differentiation, cell growth, cell recognition, and the onset of many diseases that involve malignant tumors, in living organisms.

For complex carbohydrates such as glycoproteins the sugar chains of the glycoproteins or the like are bound to the peptide chain of the glycoproteins either via N-glycosidic linkages or O-glycosidic linkages. Of these two kinds of sugar chains, the sugar chains with 0-glycosidic linkages mainly exist in blood group substances and in glycoproteins involved in immunity. It has been found that such sugar chains with 0-glycosidic linkages have a variety of important physiological functions. In order to further identify these functions, the structural investigation of the sugar chains is indispensable. For this kind of analysis of the structure of the sugar chains, the use of various glycosidases that have high substrate specificity for the sugar chain structure in complex carbohydrates provides an important means.

Of such glycosidases, endo-α-N-acetylgalactosaminidase) (endo-α-GalNAcase) can be used as an enzyme that acts on sugar chains with a Gal β1→ 3GalNAc structure in which the GalNAc is bound the serine or threonine residues of proteins, to cleave the O-glycosidic linkages; thus, the enzyme releases the sugar chains from the proteins. This action of the enzyme is shown in the following formula:

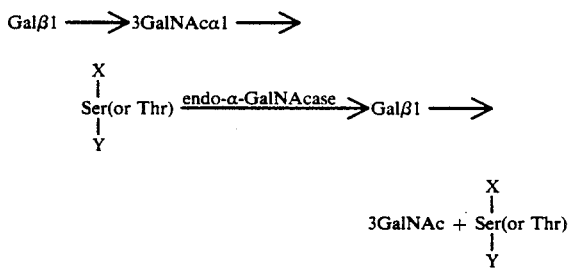

wherein Gal is galactose, GalNAc is N-acetylgalactosamine, Ser is serine, Thr is threonine, and X and Y are peptide chains. In this way, because endo-α-GalNAcase can release sugar chains with O-gylcosidic linkages from proteins, this enzyme is important for the structural analysis of the sugar chains of glycoproteins.

Previously, the activity of endo-α-GalNAcase has been found in the culture medium of *Clostridium perfringens* or *Diplococcus pneumoniae* only. Also, the purification and the characterization of this enzyme are not yet satisfactory, which decreases its practical value.

SUMMARY OF THE INVENTION

The method of producing endo-αN-acetylgalactosaminidase of this invention, which overcomes the above-discussed and numerous other disadvantages and deficiencies of the prior art, comprises the steps of growing a microorganism belonging to the genus Alcaligenes that produces enddo-αN-acetylgalactosaminidase, and isolating endo-α-N-acetylgalactosaminidase from the cultures of said microorganism.

In a preferred embodiment, the microorganism belonging to the genus *Alcaligenes* mentioned above is *Alcaligenes* sp. F-1906 (FERM BP-1857).

Accordingly, the invention described herein makes possible the objectives of (1) providing an endo-α-GalNAcase that is very useful in the structural and functional analysis of mucin-type sugar chains of glycoproteins; and (2) providing a simple method for the production of endo-α-GalNAcase inexpensively on a large scale.

DESCRIPTION OF THE PREFERRED EMBODIMENTS

The inventors of this inventions searched widely in nature for microorganisms capable of producing endo-α-GalNAcase that acts on sugar chains with O-glycosidic linkages. As a result, this microorganism isolated from soil, that had properties suitable for the purposes mentioned above.

The bacteriological characteristics of this strain are shown in the following Table 1.

TABLE 1

| Bacteriological characteristics | |
|---|---|
| (1) Morphology | |
| Shape of cells | Short rods |
| Size of cells | (0.04–0.5) × (1.2–1.8) μm |
| Mobility | None |
| Flagellation | None |
| Spores | None |
| Gram staining | Negative |
| (2) Growth on different media | |
| (a) Meat-broth agar plates | |
| Shape of colonies | Small circles |
| Upward growth | Convex curve |
| Edge | Complete |
| Surface | Glossy |
| (b) Meat-broth agar slanting medium | |
| Quality of growth | Moderate |
| Surface | Glossy |
| Condition of growth | Belt-like |
| Color | Yellowish-white when grown in a dark place, and yellow when grown in a light place |
| Gloss | Present |
| Transparency | Semi-transparent |
| (c) Meat-broth liquid medium | |
| Growth on surface | None |
| Turbidity | Moderate |
| Precipitate | Moderate |
| (d) Meat-broth gelatin stab culture | |
| Condition of growth | Grows only on surface |
| Liquification of gelatin | Weakly positive |
| (e) Litmus milk | |
| Coagulation | Negative |
| pH | Alkaline |
| (3) Physiological characteristics | |
| Reduction of nitrate | + |
| Denitrification reaction | − |
| MR test | − |
| VP test | − |
| Indole production | − |
| Hydrogen sulfide production | − |
| Starch hydrolysis | + |
| Utilization of citric acid | + |
| Utilization of inorganic nitrogen | |
| Sodium nitrate | + |
| Ammonium nitrate | + |
| Production of pigments | − |

TABLE 1-continued

| Bacteriological characteristics | |
|---|---|
| Urease | − |
| Oxidase | + |
| Catalase | + |
| Growth limits | |
| pH | 5.5–9.4 |
| Temperature | 20–37° C. |
| Oxygen requirements | Aerobic |

| Acid and gas production from sugars: | | |
|---|---|---|
| Sugars | Acid | Gas |
| L-Arabinose | − | − |
| D-Xylose | − | − |
| D-Glucose | − | − |
| D-Mannose | − | − |
| D-Fructose | − | − |
| D-Galactose | − | − |
| Maltose | − | − |
| Sucrose | − | − |
| Lactose | − | − |

| | |
|---|---|
| Growth on medium containing 5% NaCl | Weak |
| 3-Ketolactose production from lactose | − |
| Decomposition of protocatechuic acid (Cleavage at ortho or meta position) | − |
| Ability to oxidize gluconic acid | − |

This strain, with the above bacteriological characteristics, was classified and identified as a strain of the genus *Alcaligenes* by reference to Bergey's *Manual of Systematic Determinative Bacteriology* (8th edition). However, it was not possible to find any known species that had the same characteristics as those of this species. Thus, this strain was identified as a new species, and named *Alcaligenes* sp. F-1906 by the inventors. This strain has been deposited as FERM BP-1857 with the Fermentation Research Institute Agency of Industrial Science and Technology.

The endo-α-GalNAcase produced by this strain has the following enzymological and physiochemical characteristics.

(1) Action of the Enzyme

This enzyme, as shown below, acts on the sugar chains of glycoproteins and the like with O-glycosidic linkages to release Gal $\beta1\rightarrow 3$GalNAc:

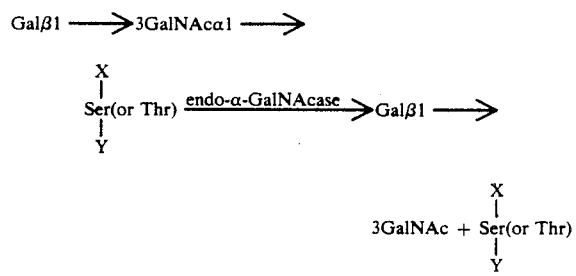

wherein X and Y are peptide chains.

(2) Substrate Specifitity

Glycopeptides or glycoproteins such as asialofetuin, asialocasein, and asialomucin, which has sugar chains with O-glycosidic linkages and Gal $\beta1\rightarrow$ 3GalNAc α→Ser (or Thr) structures can be used as substrates.

(3) Measurement of the Enzyme Activity

The activity of this enzyme can be measured with asialofetuin as a substrate. The enzyme reaction is carried out in citrate buffer, pH 4.5, at 37° C., and then stopped by adding a borate buffer, pH 9.1, to this reaction mixture. The Gal $\beta1\rightarrow$3GalNAc produced is measured by the method of Reissig. One unit of enzyme activity is defined as the amount of enzyme that releases 1 μmol of Gal $\beta1,\rightarrow$3GalNAc in one minute.

(4) Optimum pH and Range of pH Stability

The optimum pH of the enzyme reaction is 4.5–5.0 The enzyme is stable in the pH range of 4.2–6.5. thin this pH range, the activity remains about 90% or more after the enzyme is left at 1 hour at 30° C.

(5) Optimum Temperature for the Enzyme Reaction and Range of Temperature for Stability The optimum temperature for the enzyme reaction is 40–45° C. The temperature at which the enzyme is stable for 10 minutes when kept in a phosphate buffer, pH 6.0, is 30° C. or less. At 40° C., about 70% of the activity remains after such treatment.

(6) Effects of Inhibitors

The enzyme was tested for the effects of various kinds of substances. The results are shown in Table 2. The table shows that the enzyme is completely inhibited by mercury. Also, it is about 26–35% inhibited by copper ion or manganese ion. It is approximately 30% inhibited by cysteine, which is one of the SH reagents, while other SH reagents such as mercaptoethanol, N-ethylmaleimide, P-chloromercuribenzoic acid, and iodoacetic acid left the enzyme activity almost unaffected. Monosaccharides left the enzyme activity almost unaffected.

TABLE 2

| Additives | Concentration (mM) | Relative activity (%) |
|---|---|---|
| None | | 100 |
| Mg | 2.5 | 92 |
| Mn | 2.5 | 65 |
| Zn | 2.5 | 88 |
| Co | 2.5 | 95 |
| Hg | 2.5 | 0 |
| Ca | 2.5 | 109 |
| Fe | 2.5 | 104 |
| Cu | 2.5 | 74 |
| Ethylenediamine-tetraacetic acid | 2.5 | 97 |
| Cysteine | 2.4 | 68 |
| Mercaptoethanol | 2.4 | 97 |
| N-Ethylmaleimide | 2.4 | 105 |
| p-Chloromercuribenzoic acid | 2.4 | 99 |
| Iodoacetic acid | 2.4 | 109 |
| Glucose | 2.0 | 109 |
| Galactose | 2.0 | 107 |
| Glucosamine | 2.0 | 111 |
| Galactosamine | 2.0 | 106 |
| Sialic acid | 1.0 | 106 |

(7) Method for Purification

The purification of this enzyme can be done by the appropriate combination of salting-out and different kinds of chromatographic methods.

(8) Molecular Weight

The molecular weight of this enzyme was estimated to be approximately 160,000 by gel filtration on Sephadex ® G-200, and approximately 160,000 by SDS-polyacrylamide gel electrophoresis.

(9) Polyacrylamide Gel Electrophoresis

The purified enzyme gave a single band on polyacrylamide gel electrophoresis.

As the microorganism belonging to the genus *Alcaligenes* used in this invention, any microorganism that produces endo-α-GalNAcase can be used. The *Alcaligenes* sp. F-1906 (FERM BP-1857) isolated by the inventors from soil is preferably used.

For the production of endo-α-GalNAcase by the microorganisms, the culture medium with mucin from pig gastric mucosa treated in 1 N sulfuric acid for one hour at 80° C. can be used. The concentration of mucin is 0.1-10%, and preferably 0.5-5%. The enzyme is produced by the aerobic culture of the microorganisms in such medium for about 48 hours at pH 6.5 and 28° C.

After the culture, the endo-α-GalNAcase can be collected and purified from the culture by a appropriate combination of known methods. Because this enzyme is secreted into the culture medium, the culture is centrifuged to remove the cells and the supernatant is fractionated with ammonium sulfate followed by ionexchange chromatography, gel filtration chromatography, affinity chromatography, etc., to purify the enzyme. The following example will illustrate the invention more precisely, but is not intended to limit the invention.

EXAMPLES

Example 1

Commercially available mucin from pig gastric mucosa was mixed with 1 N sulfuric acid and left for 1 hour at 80° C. for hydrolysis, which removed the sialic acid moiety of the mucin. The hydrolysate was added to the medium at the concentration of 1%. Five hundred milliliters of the medium was put into each of 40 flasks with a capacity of 2 liters, which were sterilized and were inoculated with 5 ml of pre-cultured Alcaligenes sp. F-1906. The flasks were cultured at 28° C. for 3 days. After the culture, the bacterial cells were removed by centrifugation, and the supernatant of the culture was obtained. Ammonium sulfate was added to this supernatant at 0-5° C. and the fractions that precipitated at the saturation of 40-80% ammonium sulfate were collected. This precipitate was dissolved in 0.01 M phosphate buffer, pH 6.0, and then dialyzed overnight against the same buffer. The dialysate was put on a DEAE-Sephadex ® A-50 column (5.0×32.5 cm) equilibrated with 0.01 M phosphate buffer. After the column was washed with the same buffer containing 0.2 M NaCl, the enzyme was eluted with the same buffer containing 0.4 M NaCl. The fractions with enzyme activity were concentrated by precipitation with ammonium sulfate at the saturation of 80%, and dialyzed overnight against 0.01 M phosphate buffer, pH 6.0. The dialysate was then put on a hydroxyapatite column (2.0 x 20 cm) equilibrated with the same buffer. The column was washed with the same buffer and with 0.4 M phosphate buffer, pH 6.0, and then eluted with 0.5 M phosphate buffer, pH 6.0. The fractions with enzyme activity were collected, concentrated by ultra-filtration, and gel filtered on a Sephadex ® G-200 column (1.0×110 cm) equilibrated with 0.01 M phosphate buffer, pH 6.0, containing 0.2 M NaCl. The fractions with enzyme activity were collected, concentrated, and put on a Con A Sepharose ® column (0.5×3 cm) equilibrated with 0.05 M phosphate buffer, pH 6.0. The fractions with enzyme activity were eluted as the fractions that did not adsorb to the column with the same buffer, and 3 mg of endo-α-GalNAcase was obtained in purified form (relative activity, 2.2 units/mg; yield, 1.0%).

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A method of producing endo-α-N-acetyl-galactosaminidase comprising the steps of growing a microorganism having all of the identifying characteristics of *Alcaligenes* sp. F-1906 and isolating endo-α-N-acetyl-galactosaminidase from the culture of said microorganism.

2. A method of producing endo-α-N-acetyl-galactosaminidase according to claim 1, wherein said microorganism is Alcaligenes sp. F-1906 (FERM BP-1857).

* * * * *